(12) United States Patent
Liu (10) Patent No.: US 9,877,512 B2
(45) Date of Patent: Jan. 30, 2018

(54) BATTERY ASSEMBLY AND ATOMIZING ASSEMBLY OF ELECTRONIC CIGARETTE, AND ELECTRONIC CIGARETTE

(71) Applicant: KIMREE HI-TECH INC., Tortola (VG)

(72) Inventor: Qiuming Liu, Shenzhen (CN)

(73) Assignee: HUIZHOU KIMREE TECHNOLOGY CO., LTD. SHENZHEN BRANCH, Guangdong (CN)

( * ) Notice: Subject to any disclaimer, the term of this patent is extended or adjusted under 35 U.S.C. 154(b) by 0 days.

(21) Appl. No.: 14/356,416

(22) PCT Filed: Nov. 25, 2013

(86) PCT No.: PCT/CN2013/087754
§ 371 (c)(1),
(2) Date: May 6, 2014

(87) PCT Pub. No.: WO2015/043048
PCT Pub. Date: Apr. 2, 2015

(65) Prior Publication Data
US 2016/0374392 A1    Dec. 29, 2016

(30) Foreign Application Priority Data
Sep. 29, 2013   (CN) .................... 2013 2 0609603 U (51) Int. Cl.
*A61H 33/12* (2006.01)
*A24F 47/00* (2006.01)
*H02J 7/00* (2006.01)

(52) U.S. Cl.
CPC .......... *A24F 47/008* (2013.01); *H02J 7/0052* (2013.01)

(58) Field of Classification Search
CPC ...... A24F 47/00; A24F 47/002; A24F 47/004; A24F 47/006; A24F 47/008;
(Continued)

(56) References Cited

U.S. PATENT DOCUMENTS

2013/0220315 A1* 8/2013 Conley ................ A61M 11/042
128/202.21
2014/0096781 A1 4/2014 Sears et al.
(Continued)

FOREIGN PATENT DOCUMENTS

| CN | 203152489 | | 8/2013 |
|----|-----------|---|--------|
| JP | 2010062969 | | 3/2010 |
| JP | 2010062969 A | * | 3/2010 |

OTHER PUBLICATIONS

Extended European Search Report dated May 12, 2017 for European application No. 13894908.6.

*Primary Examiner* — Quang D Thanh
*Assistant Examiner* — Brandon Harvey
(74) *Attorney, Agent, or Firm* — Ohlandt, Greeley, Ruggiero & Perle, LLP (57) ABSTRACT

A battery assembly for an electronic cigarette, configured to form an electronic cigarette in combination with an atomizing assembly, wherein the atomizing assembly is provided with a magnetic material containing information to be identified, and the battery assembly includes: a magnetic sensor arranged on the battery assembly and configured to obtain the information to be identified; and a microcontroller connected to the magnetic sensor, and configured to control a circuit between the battery assembly and the atomizing assembly to be switched on in a case that the microcontroller determines that the information to be identified matches a preset information, to enable the electronic cigarette to work normally.

11 Claims, 10 Drawing Sheets (58) Field of Classification Search
CPC ....... H02J 2007/0001; H02J 2007/0009; H02J 7/0009; H02J 7/0052
USPC ........................................ 392/386, 394, 404
See application file for complete search history.

(56) References Cited

U.S. PATENT DOCUMENTS

2014/0332019 A1* 11/2014 Liu ..................... A61M 15/06
   131/329
2014/0334804 A1* 11/2014 Choi .................... A61M 15/06
   392/404

* cited by examiner

BATTERY ASSEMBLY AND ATOMIZING ASSEMBLY OF ELECTRONIC CIGARETTE, AND ELECTRONIC CIGARETTE

The present application is the national phase of International Application No. PCT/CN2013/087754, titled "BATTERY ASSEMBLY AND ATOMIZING ASSEMBLY OF ELECTRONIC CIGARETTE, AND ELECTRONIC CIGARETTE", filed on Nov. 25, 2103, which claims the benefit of priority to Chinese Patent Application No. 201320609603.2 titled "BATTERY ASSEMBLY AND ATOMIZING ASSEMBLY OF ELECTRONIC CIGARETTE, AND ELECTRONIC CIGARETTE", filed with Chinese State Intellectual Property Office on Sep. 29, 2013 both of which applications are incorporated herein in their entireties by this reference.

TECHNICAL FIELD

The present application relates to the technical field of electronic cigarettes, and particularly to a battery assembly and an atomizing assembly of an electronic cigarette, and an electronic cigarette.

BACKGROUND

Figure 1:
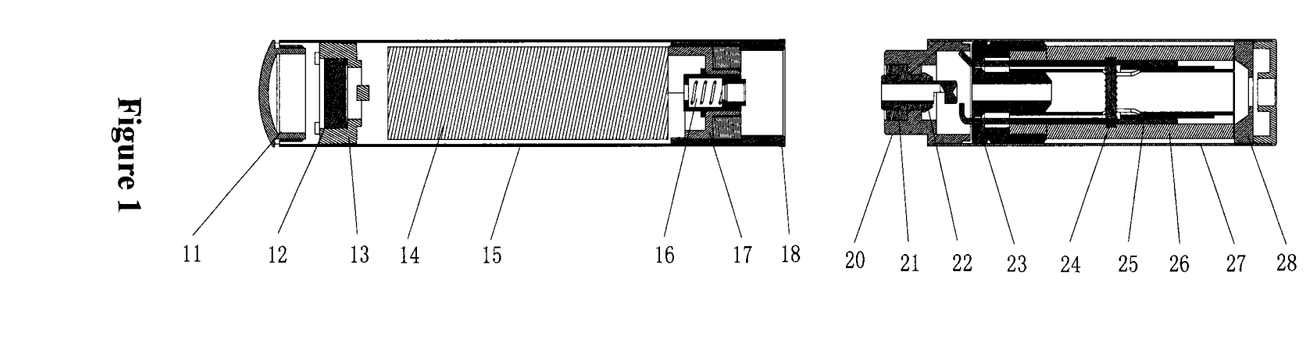
FIG. 1 is a schematic view showing the structure of an electronic cigarette in the conventional technology.

An existing electronic cigarette mainly includes a battery assembly and an atomizing assembly, the structure of which is shown in FIG. 1. The battery assembly includes an end cap 11, a microphone controller 12, a microphone seat 13, a battery 14, a battery sleeve 15, a lower electrode 16, an electrode fixing seat 17 and a connecting seat 18. The atomizing assembly includes a connector 20, an upper electrode 21, an upper insulating ring 22, an atomizing seat 23, an atomizing device 24, a PVC fiberglass sleeving 25, a liquid storage cotton 26, an atomizing sleeve 27 and a mouthpiece cover 28.

In conjunction with FIG. 1, the electronic cigarette can work normally by connecting the connecting seat 18 in the battery assembly to the connector 20 in the atomizing assembly. The inventor found that, the existing electronic cigarettes may be used in combination as long as connectors of the battery assembly and the atomizing assembly can be connected, irrespective of brands of the electronic cigarettes. Thus, when the battery assembly and the atomizing assembly, which are not matched, are used in combination, the power of the heating wire in the atomizing device does not match the power of the battery, which may cause damages to the electronic cigarette, for example battery overheat or battery leakage, and may further shorten the service life of the electronic cigarettes. Since the existing battery assembly and atomizing assembly can be used in any combination, it is apt to cause the mixed use of tobacco liquids having different flavors and the mixed use of the battery assembly and the atomizing assembly from different manufacturers, which may cause a poor user experience, hinders a user from knowing about the manufacturers and the brands, and is not beneficial for the user to quit smoking.

SUMMARY

In view of this, a battery assembly and an atomizing assembly of an electronic cigarette, and an electronic cigarette are provided according to the present application, which may effectively solve the problem in the conventional technology that damages on the electronic cigarette, for example battery overheat or battery leakage, may be caused in a case that the battery assembly and the atomizing assembly, which are not matched, are used in combination.

To achieve the above object, the present application provides the following technical solutions.

A battery assembly for an electronic cigarette, configured to form an electronic cigarette in combination with an atomizing assembly, wherein the atomizing assembly is provided with a magnetic material containing information to be identified, and the battery assembly includes:

a magnetic sensor arranged on the battery assembly and configured to obtain the information to be identified; and a microcontroller connected to the magnetic sensor, and configured to control a circuit between the battery assembly and the atomizing assembly to be switched on in a case that the microcontroller determines that the information to be identified matches a preset information, to enable the electronic cigarette to work normally.

Preferably, the magnetic sensor is a magnetic head and/or a Hall sensor.

Preferably, the battery assembly further includes a power supply management circuit, arranged between a battery and a magnetic information identification circuit in the battery assembly and configured to manage charging the battery via an external power supply.

Preferably, the battery assembly further includes a notification device, electrically connected to the microprocessor and configured to show a matching result from the microprocessor, and the notification device is an alarm or an indicator light.

An atomizing assembly for an electronic cigarette, configured to form an electronic cigarette in combination with a battery assembly, wherein the atomizing assembly is provided with a magnetic material containing information to be identified and configured to match the battery assembly.

Preferably, the information to be identified of the magnetic material includes a magnetic strength and a magnetic signal.

Preferably, the atomizing assembly is provided with an upper electrode configured to be electrically connected with the battery assembly, and the upper electrode is provided with an outer electrode and an inner electrode which are sleevedly engaged, and the magnetic material to be identified is arranged on the inner electrode.

An electronic cigarette, including a battery assembly and an atomization assembly, and the battery assembly may be any one of the battery assemblies described above; and the atomizing assembly may be any one of the atomizing assemblies described above.

Based on the above technical solutions, compared to the conventional technology, a battery assembly for an electronic cigarette, configured to form an electronic cigarette in combination with an atomizing assembly, is provided according to the present application. The atomizing assembly is provided with a magnetic material to be identified, and the battery assembly is provided with a magnetic sensor and a microcontroller, wherein the magnetic sensor is configured to obtain the information to be identified, and the microcontroller is configured to control a circuit between the battery assembly and the atomizing assembly to be switched on in a case that the magnetic information identification circuit determines that the information to be identified matches a preset information, to enable the electronic cigarette to work normally.

Thus, the electronic cigarette has an identification function and can be normally used only when the battery assembly and the atomizing assembly of the electronic cigarette are matched, thereby avoiding the problem that damages on the electronic cigarette, for example battery overheat or battery leakage, are caused in a case that the battery assembly and the atomizing assembly, which are not matched, are used in combination. In addition, the present application also avoids a poor user experience resulting from the mixed use of the existing battery assembly and atomizing assembly in any combination, the mixed use of tobacco liquids having different flavors, and the mixed use of the battery assembly and the atomizing assembly from different manufacturers.

BRIEF DESCRIPTION OF THE DRAWINGS

In order to more clearly illustrate the embodiments of the present application or the prior art solution, the drawings used in the description of embodiments or the prior art will be made in following, obviously the drawings in following description only are embodiments of the present application, and for the skilled person of the prior art, it is also possible to obtain other drawings based on the provided drawings without creative efforts.

REFERENCE NUMERALS

| 11 end cap, | 12 microphone controller, |
|---|---|
| 13 microphone seat, | 14 battery, |
| 15 battery sleeve, | 16 lower electrode, |
| 17 electrode fixing seat, | 18 connecting seat, |
| 19 magnetic sensor, | 20 connector, |
| 21 upper electrode, | 22 upper insulating ring, |
| 23 atomizing seat, | 24 atomizing device, |

-continued

| 25 PVC fiberglass sleeving, | 26 liquid storage cotton, |
|---|---|
| 27 atomizing sleeve, | 28 mouthpiece cover, |
| 29 magnetic material, | 30 lower insulating ring, |
| 21a upper outer electrode, | 21b upper inner electrode, |
| 16a lower outer electrode, and | 16b lower inner electrode. |

DETAILED DESCRIPTION

A battery assembly and an atomizing assembly of an electronic cigarette, and an electronic cigarette are provided according to the present application, wherein the electronic cigarette has an image identification function to ensure that the electronic cigarette can be normally used only when the battery assembly and the atomizing assembly are matched, thereby avoiding damage to connectors of the electronic cigarette caused by mismatching, and avoiding unnecessary troubles caused by interchange between connectors of electronic cigarettes in different brands.

The technical solutions in the embodiments of the present application will be described clearly and completely hereinafter in conjunction with the drawings in the embodiments of the present application. Apparently, the described embodiments are only a part of the embodiments of the present application, rather than all embodiments. Based on the embodiments in the present application, all of other embodiments, made by the person skilled in the art without any creative efforts, fall into the protection scope of the present application.

First Embodiment

Figure 2:
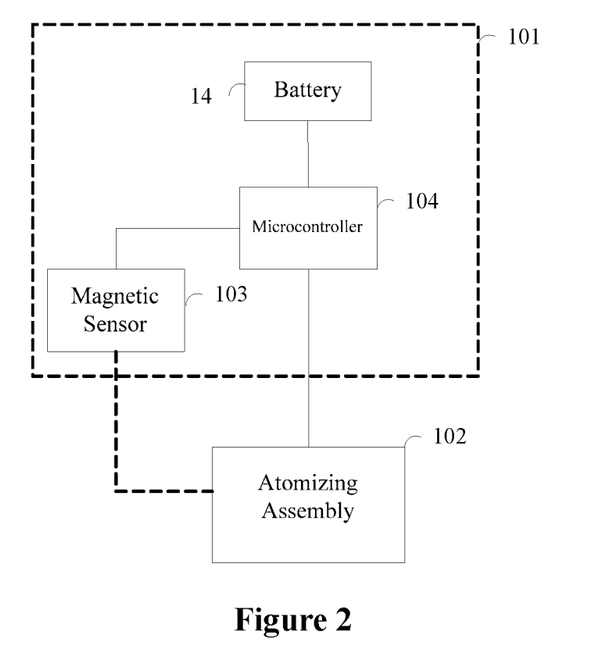
FIG. 2 is a functional block diagram of a battery assembly of an electronic cigarette according to an embodiment of the present application.

Referring to FIG. 2, a battery assembly 101 of an electronic cigarette according to an embodiment of the present application is adapted to form an electronic cigarette in combination with an atomizing assembly 102. The atomizing assembly 102 is provided with a magnetic material containing information to be identified, and the battery assembly 101 includes a magnetic sensor 103 and a microcontroller 104.

The magnetic sensor 103 is configured to obtain the information to be identified of the magnetic material. The microcontroller 104 is connected to the magnetic sensor 103, and is configured to determine whether the information to be identified matches a preset information, and in a case that the information to be identified matches the preset information, the microcontroller 104 controls a circuit between the battery assembly and the atomizing assembly to be switched on to enable the electronic cigarette to work normally; and in a case that the information to be identified does not match the preset information, the microcontroller 104 controls the circuit between the battery assembly and the atomizing assembly to be switched off to power off the electronic cigarette, that is, the electronic cigarette cannot work at this time.

Thus, the electronic cigarette has an identification function and can be normally used only when the battery assembly and the atomizing assembly of the electronic cigarette are matched, thereby avoiding the problem that damages on the electronic cigarette, for example battery overheat or battery leakage, are caused in a case that the battery assembly and the atomizing assembly, which are not matched, are used in combination. In addition, the present application also avoids a poor user experience resulting from the mixed use of the existing battery assembly and atomizing assembly in any combination, the mixed use of tobacco liquids having different flavors, and the mixed use of the battery assembly and the atomizing assembly from different manufacturers.

Preferably, in this embodiment, the magnetic sensor 103 may be a magnetic head. It should be noted that, the magnetic head may be selected according to actual needs, for example various parameters of the magnetic head should be taken into consideration, such as size, shape, and performance. The working principle of the magnetic sensor 103 may be the same as that of the magnetic head of a hard disk or a recorder, but is not limited to this. The magnetic head of the present application may be a device capable of converting magnetic information into an electrical signal.

Figure 3:
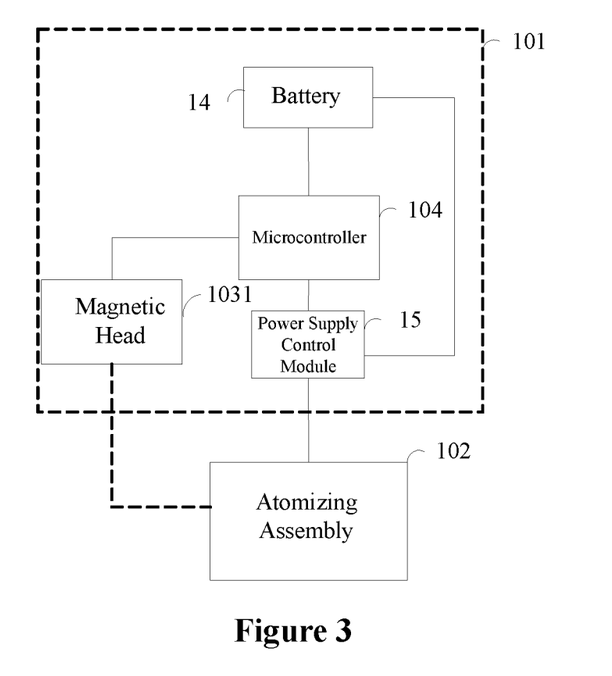
FIG. 3 is a functional block diagram of an electronic cigarette in the present application.

Referring to FIG. 3, the structure and working principle of the electronic cigarette according to this embodiment are described briefly hereinafter by taking the magnetic sensor 103 being a magnetic head 1031 having the same working principle as the magnetic head of the hard disk as an example.

The battery assembly of the electronic cigarette is provided with the magnetic head 1031, and the atomizing assembly is provided with a micro storable magnetic material containing predetermined information. When a connector of the battery assembly is rotated into a connector of the atomizing assembly to be connected to the connector of the atomizing assembly, the magnetic head 1031 in the battery assembly may detect a variable magnetic signal on the atomizing assembly. At this time, the magnetic head 1031 converts the variable magnetic signal into an electric signal and sends the electric signal to the microcontroller. In a case that the microcontroller identifies a correct signal, the microcontroller outputs a control signal to activate a power supply control module 15 in the battery assembly, that is, a circuit between the battery assembly and the atomizing assembly of the electronic cigarette is switched on, thus the electronic cigarette may work normally. The power supply control module may be a field-effect tube or a triode electrically connected to the battery of the battery assembly and the heating wire of the atomizing assembly.

In a case that the information identified by the microcontroller does not match the preset information, the power supply control module will not be activated, that is, the circuit between the battery assembly and the atomizing assembly is switched off, and the battery assembly cannot supply power to the atomizing assembly, thus the electronic cigarette cannot work normally. In this embodiment, the processor will automatically reset when charging the battery, thus it is necessary to rotate the atomizing assembly again to identify the signal before the electronic cigarette can be used normally. In this way, the mixed use of the atomizing assembly with other specifications or brands may be avoided. It should be noted that, in this embodiment the pre-stored company information is written by manufacturers by themselves, and the content of the information is not limited herein.

On the basis that the magnetic sensor 103 is the magnetic head 1031 having the same working principle as the magnetic head of the hard disk, this embodiment may also identify the electronic cigarette by changing the connection manner between the atomizing assembly and the battery assembly, and detailed operations are described as follows.

When a connector of the battery assembly is rotated into a connector of the atomizing assembly in a clockwise direction to be connected to the connector of the atomizing assembly, the magnetic head 1031 in the battery assembly detects a variable magnetic signal on the atomizing assembly. The magnetic sensor 103 converts the variable magnetic signal into an electrical signal and sends the electrical signal to the microcontroller, at this time, in a case that the microcontroller identifies a correct signal, the microcontroller outputs a high level control signal '1' to activate a power supply control module in the battery assembly, thus the electronic cigarette may work normally. When the connector of the battery assembly is rotated into the connector of the atomizing assembly in an anti-clockwise direction to be connected to the connector of the atomizing assembly, the magnetic sensor 103 in the battery assembly detects the variable magnetic signal on the atomizing assembly. The magnetic sensor 103 converts the variable magnetic signal into an electrical signal and sends the electrical signal to the microcontroller, and at this time, in a case that the microcontroller identifies a correct signal, the microcontroller outputs a low level control signal '0' to deactivate the power supply control module in the battery assembly, thus the electronic cigarette stops working.

Second Embodiment

Figure 4:
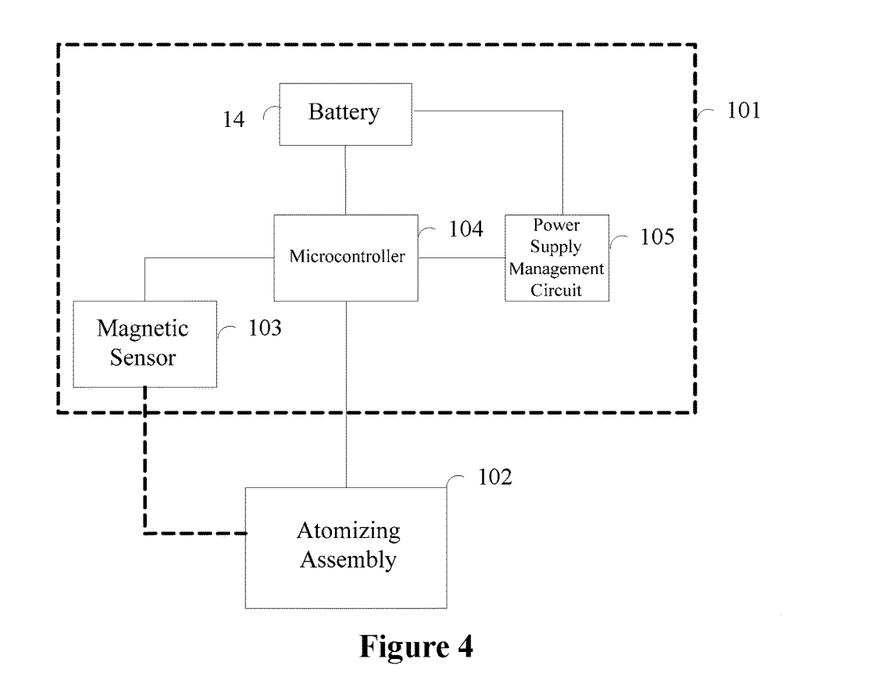
FIG. 4 is a functional block diagram of another electronic cigarette in the present application.

Reference is made to FIG. 4, wherein the electronic cigarette of another structure according to this embodiment is shown. A power supply management circuit 105 is added in this embodiment. The electronic cigarette in this embodiment includes a battery assembly 101 and an atomizing assembly 102. The battery assembly 101 includes a magnetic sensor 103, a microcontroller 104 and the power supply management circuit 105. The power supply management circuit 105 is configured to manage charging a battery 14 via an external power supply. The working principle of other parts in this embodiment is the same as the above embodiment, thus will not be described in detail herein.

Figure 5:
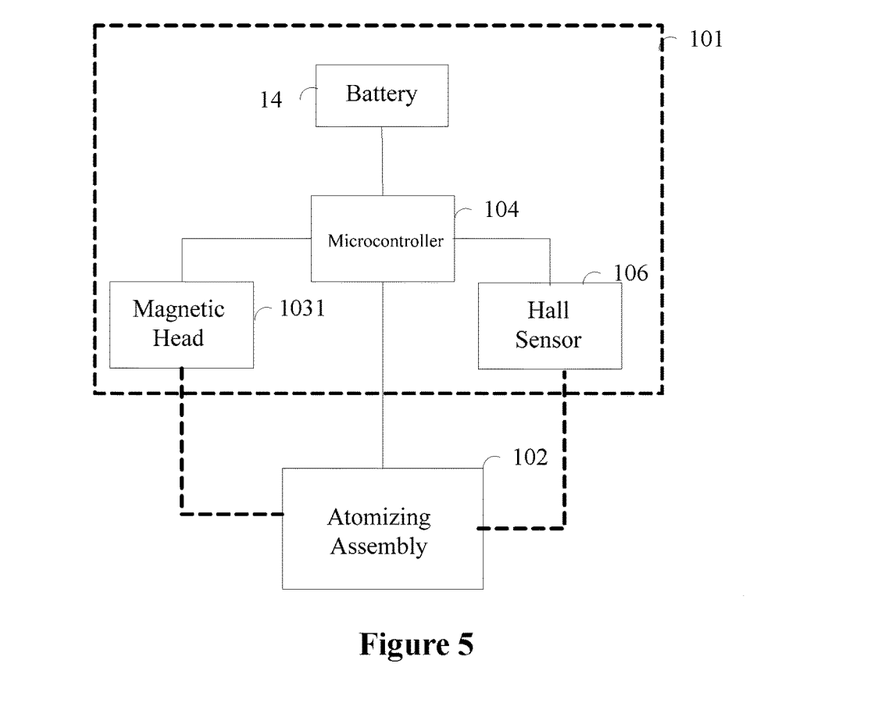
FIG. 5 is a functional block diagram of another electronic cigarette in the present application.

Referring to FIG. 5, on the basis of the first embodiment, the second embodiment provides the battery assembly which includes a magnetic head 1031, a hall sensor 106 and a microcontroller 104.

The working principle is described as follows. The magnetic head (such as a magnetic head of a hard disk) and the Hall sensor are installed in a battery rod, and the atomizer is provided with a micro storage magnetic material containing pre-stored company information. When a connector in the battery rod is rotated into a connector of the atomizer to be connected to the connector of the atomizer, the magnetic head in the battery rod detects a variable magnetic signal on the atomizer, and at the same time, the Hall element also detects the magnetic signal. The magnetic head converts the variable magnetic signal into an electric signal and sends the electric signal to the processing microcontroller, and the Hall sensor also outputs a control signal to the processor at the same time. In a case that the processing microcontroller identifies a correct signal, the processing microcontroller outputs a control signal '1', then the control signal '1' from the processing microcontroller and a control signal '1' from the Hall sensor are entered into an AND gate circuit to generate a main control signal '1' for activating the power supply control module in the battery rod, thus the electronic cigarette may work normally. In a case that the processing microcontroller identifies wrong information (only containing magnetic field without data), the processing microcontroller will not activate the power supply control module, thus the atomizer is not powered, and the electronic cigarette cannot work normally.

Third Embodiment

Figure 6:
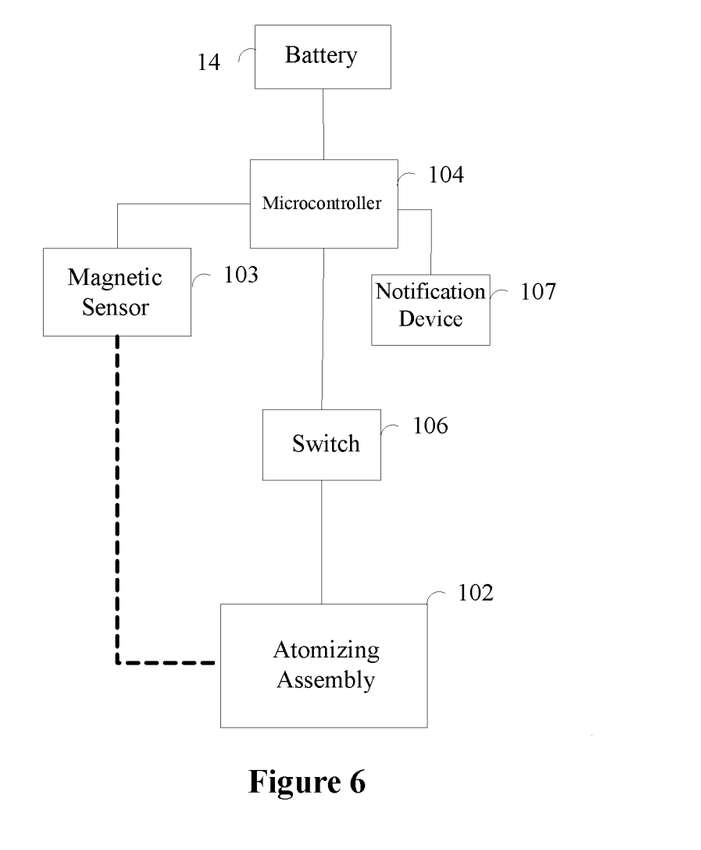
FIG. 6 is a functional block diagram of another electronic cigarette in the present application.

Referring to FIG. 6, a battery assembly of an electronic cigarette according to this embodiment of the present application is adapted to form an electronic cigarette in combination with an atomizing assembly 102. The battery assembly includes a magnetic sensor 103, a microprocessor 104 and a switch 106.

The magnetic sensor 103 is configured to obtain information to be identified of a magnetic material. The microcontroller 104 is connected to the magnetic sensor 103, and is configured to determine whether the information to be identified matches a preset information, and in a case that the information to be identified matches the preset information, the microcontroller 104 controls a circuit between the battery assembly and the atomizing assembly to be switched on, and at this time, the switch 106 is pressed, then the electronic cigarette may work normally. In a case that the information to be identified does not match the preset information, the microcontroller controls the circuit between the battery assembly and the atomizing assembly to be switched off to power off the electronic cigarette, that is, the electronic cigarette cannot work Normally.

It should be noted that, the switch 106 may be a pneumatic sensor switch or a mechanical switch. Preferably, this embodiment also provides a device 107 for notifying identification result. The device is electrically connected to the microprocessor, and is configured to notify the identification result of the microprocessor. The device may be an alarm or an indicator light, and the alarm may be a buzzer alarm, a loudspeaker or the like.

Thus, the electronic cigarette has an identification function and can be normally used only when the battery assembly and the atomizing assembly of the electronic cigarette are matched, thereby avoiding the problem that damages on the electronic cigarette, for example battery overheat or battery leakage, are caused in a case that the battery assembly and the atomizing assembly, which are not matched, are used in combination. In addition, the present application also avoids a poor user experience resulting from the mixed use of the existing battery assembly and atomizing assembly in any combination, the mixed use of tobacco liquids having different flavors, and the mixed use of the battery assembly and the atomizing assembly from different manufacturers.

Fourth Embodiment

In addition to the above embodiments, this embodiment further provides an atomizing assembly of an electronic cigarette, and a magnetic material to be identified is arranged on an upper electrode of the atomizing assembly at a position close to a battery assembly. In this embodiment, the upper electrode is provided with an outer electrode and an inner electrode which are sleevedly engaged, and the magnetic material to be identified is arranged on the inner electrode.

According to this embodiment, an electronic cigarette may be formed by combining the atomizing assembly with the battery assembly. Therefore, this embodiment further provides an electronic cigarette including the battery assembly and the atomizing assembly, and the battery assembly includes the microcontroller and the magnetic sensor described in any one of the above embodiments, and a magnetic material to be identified is arranged on an upper electrode of the atomizing assembly at a position close to the battery assembly.

Referring to FIGS. 6 to 13, three types of installation position of the magnetic sensor and the microcontroller according to this embodiment are shown. Certainly, the installation positions are not limited to this, and the positions introduced here are only exemplary.

In FIG. 6, a magnetic material 29 is mounted at a top portion of a connecting part of the atomizing assembly, and accordingly, a magnetic sensor 19 is arranged at a top portion of the battery assembly. After the atomizing assembly and the battery assembly are connected by threads, the magnetic sensor reads the information to be identified in the magnetic material of the atomizing assembly, and in a case that the information to be identified matches with a preset information, the electronic cigarette is enabled to work normally.

Figure 7:
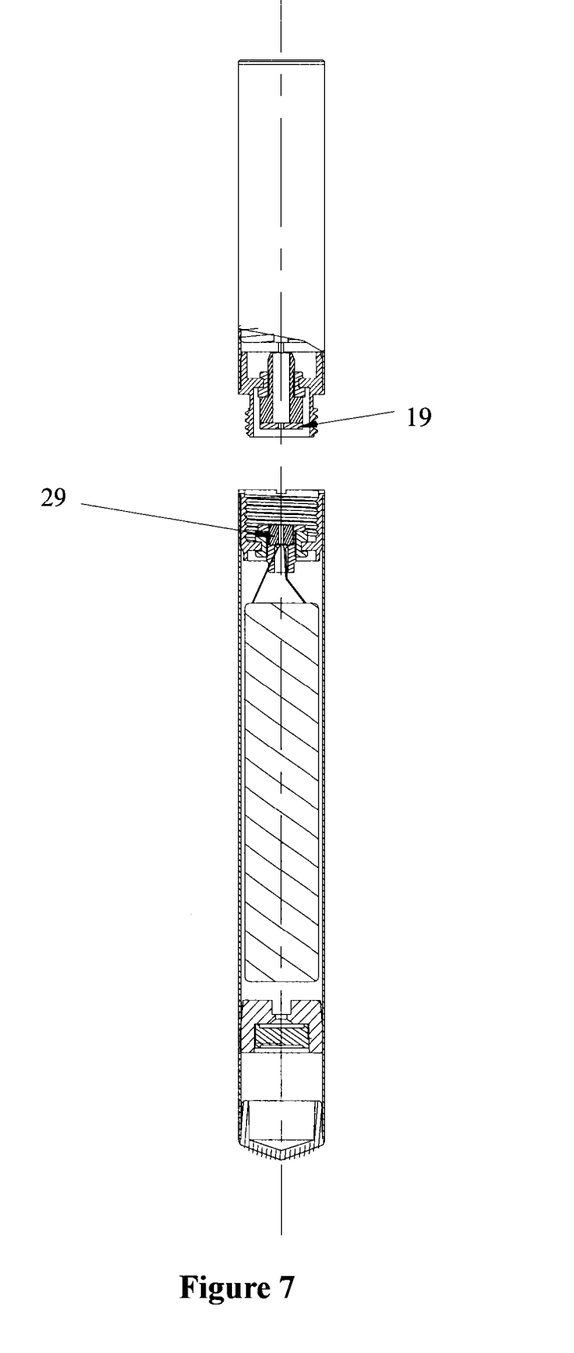
FIG. 7 is an installation schematic view of a magnetic information identification circuit according to the embodiment of the present application.
Figure 8:
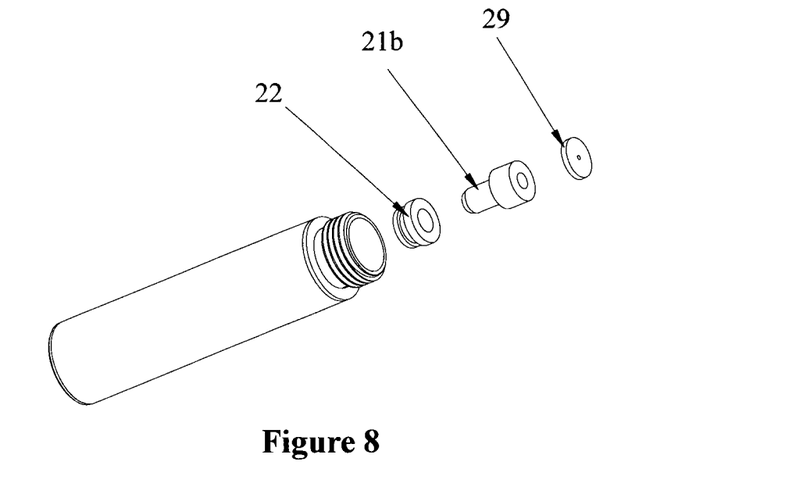
FIG. 8 is a schematic view showing the structure of an atomizing assembly in FIG. 7.

The atomizing assembly is shown in FIG. 7, the magnetic material 29 is mounted on an end surface, close to the battery assembly, of an upper inner electrode 21b, and an insulating ring 22 is sleeved on the upper inner electrode 21b, and the upper inner electrode 21b is mounted in the atomizing assembly. Accordingly, the battery assembly is shown in FIG. 8, the magnetic sensor 19 is mounted on an end surface of a lower inner electrode 16b, and the lower inner electrode 16b is mounted in the battery assembly via a lower insulating ring 30.

Figure 9:
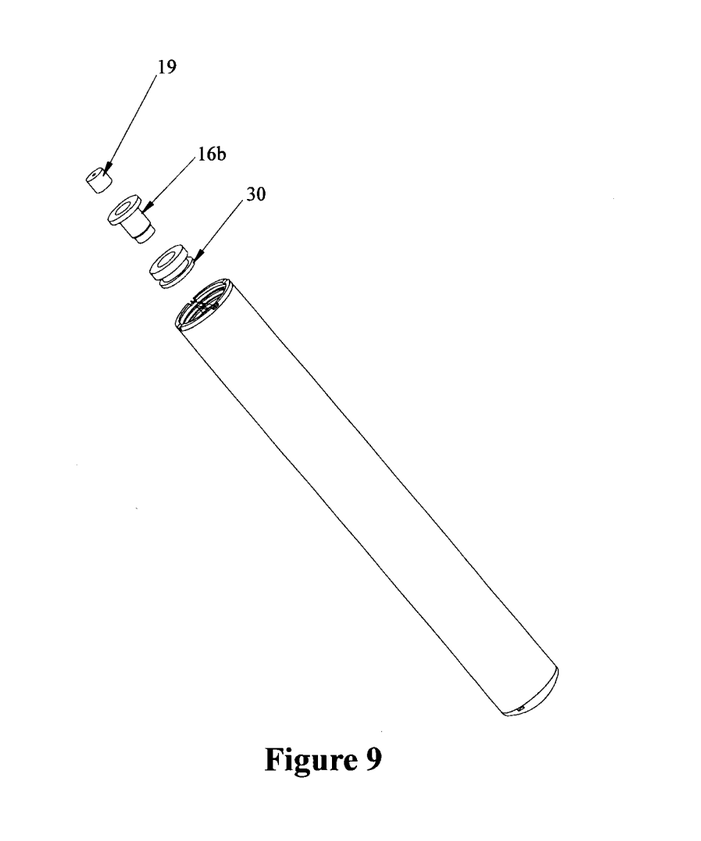
FIG. 9 is a schematic view showing the structure of a battery assembly in FIG. 7.

The second installation manner is shown in FIG. 9. The magnetic material 29 is arranged on an electrode surface of an outer electrode 21 of the atomizing assembly (i.e., the outer electrode of the upper electrode). Correspondingly, the magnetic sensor 16 is arranged on an inner surface of a bracket of the battery assembly. After the atomizing assembly is inserted into the battery assembly and then is rotated into the battery assembly to be fixed to the battery assembly, the magnetic sensor reads the information to be identified in the magnetic material of the atomizing assembly, and in a case that the information to be identified is accurate, the electronic cigarette may work normally; otherwise, the electronic cigarette does not work.

Figure 10:
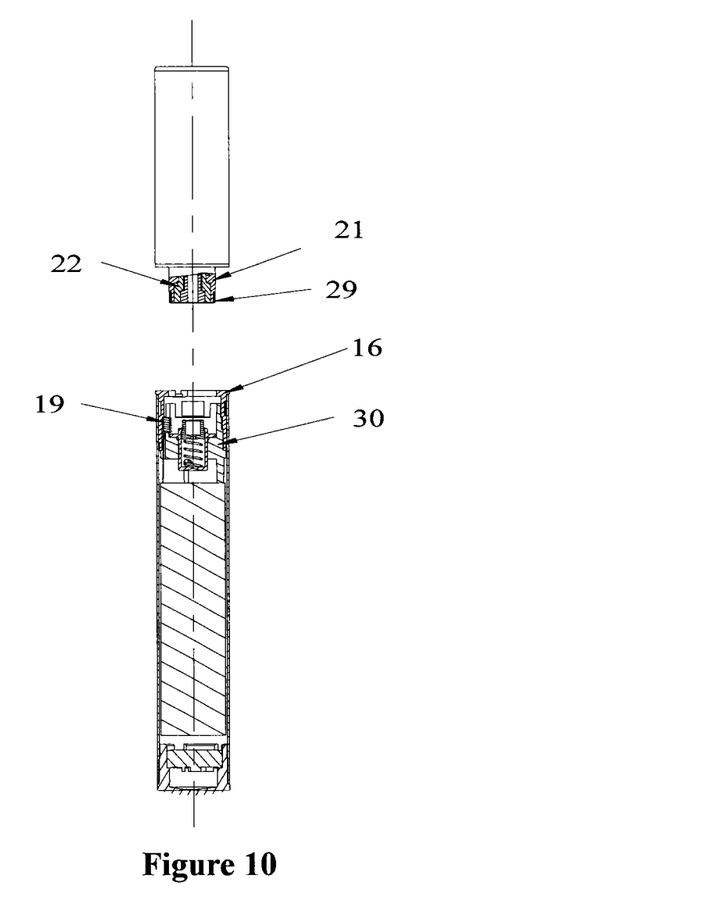
FIG. 10 is another installation schematic view of the magnetic information identification circuit according to the embodiment of the present application.
Figure 11:
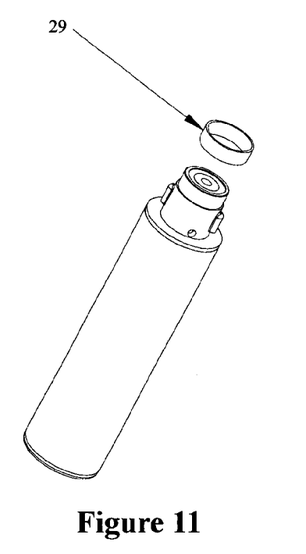
FIG. 11 is a schematic view showing the structure of an atomizing assembly in FIG. 10.

The atomizing assembly is shown in FIG. 10, and the magnetic material 29 is arranged on a top portion of the atomizing assembly. The battery assembly is shown in FIG. 11, the upper inner electrode 21b is arranged in an upper outer electrode 21a, and the upper electrode 21 is mounted in the battery assembly via the lower insulating ring 30. In this embodiment, the magnetic sensor 19 is mounted on the lower insulating ring at a portion where the lower insulating ring is connected to a pipe sleeve of the battery assembly, that is, the inner surface of the bracket of the battery assembly.

Figure 12:
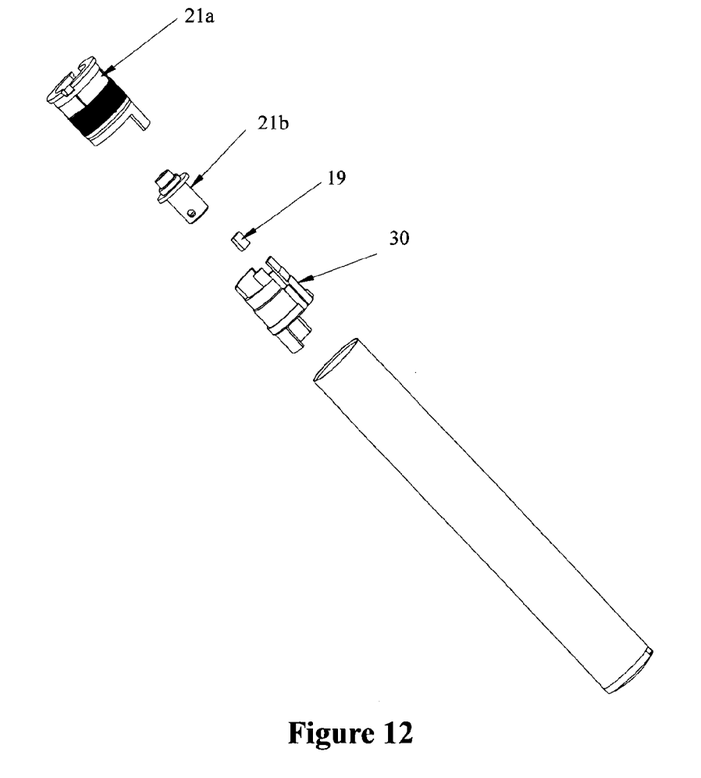
FIG. 12 is a schematic view showing the structure of a battery assembly in FIG. 10.

The third installation manner according to the present application is shown in FIG. 12, and the atomizing assembly is provided with a magnetic material, and correspondingly, the magnetic sensor 19 is arranged on an end cover 14 (a lamp cap) of the battery assembly. Before the atomizing assembly is connected to the battery assembly, the magnetic material of the atomizing assembly is placed adjacent to the end cover of the battery assembly, and at this time, the magnetic sensor reads the information to be identified of the magnetic material on the atomizing assembly, and in a case that the information to be identified is accurate, the electronic cigarette may work normally; otherwise, the electronic cigarette does not work.

Figure 13:
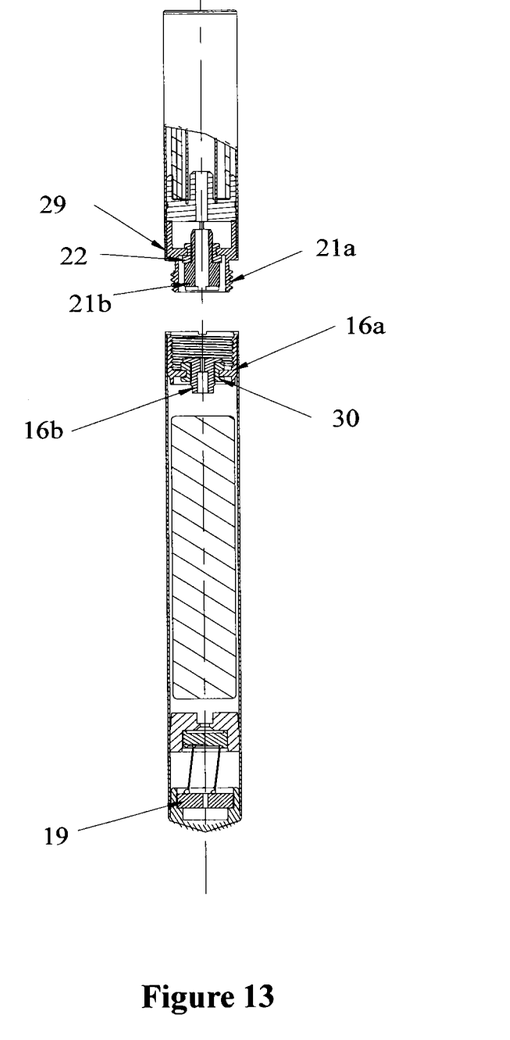
FIG. 13 is another installation schematic view of the magnetic information identification circuit according to the embodiment of the present application.
Figure 14:
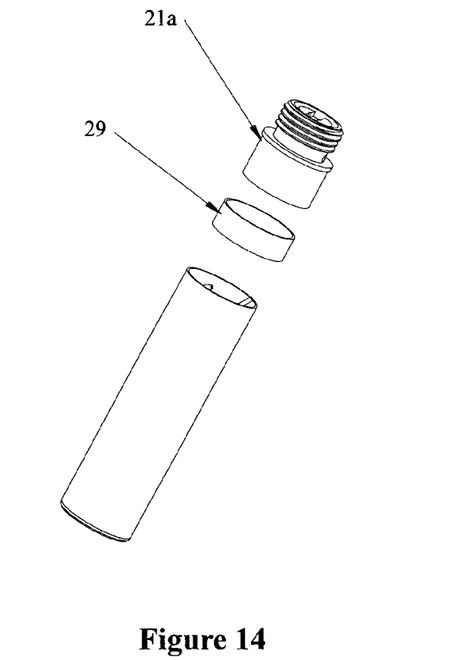
FIG. 14 is a schematic view showing the structure of an atomizing assembly in FIG. 13.
Figure 15:
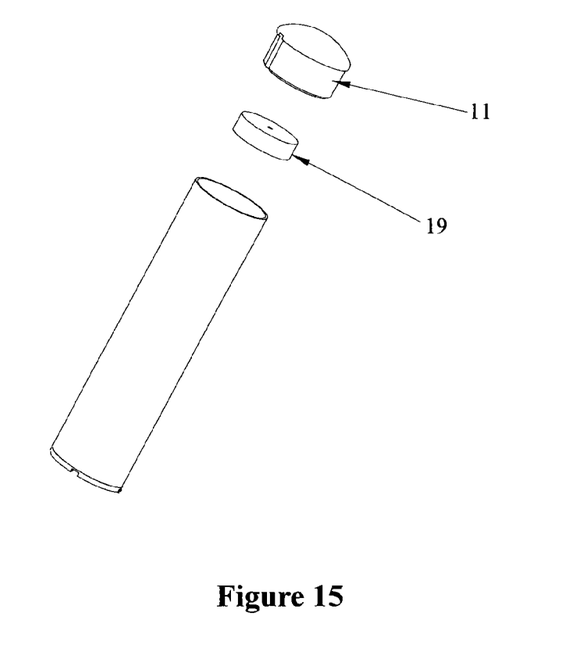
FIG. 15 is a schematic view showing the structure of a battery assembly in FIG. 13.

The atomizing assembly 13 is shown in FIG. 13, and the magnetic material 29 is arranged between the upper outer electrodes 21a and other components of the atomizing assembly. Correspondingly, the battery assembly is shown in FIG. 14, and the magnetic sensor 19 is arranged at the end cover 11.

In summary, a battery assembly of an electronic cigarette according to the present application is adapted to form an electronic cigarette in combination with an atomizing assembly. The atomizer of the electronic cigarette is provided with a magnetic material to be identified, and the battery assembly includes a magnetic sensor and a microcontroller. The magnetic sensor is configured to obtain information to be identified of the magnetic material. The microcontroller is configured to determine whether the information to be identified matches a preset information, and in a case that the information to be identified matches the preset information, the microcontroller controls a circuit between the battery assembly and the atomizing assembly to be switched on to enable the electronic cigarette to work normally. Thus, the electronic cigarette has an identification function and can be normally used only when the battery assembly and the atomizing assembly of the electronic cigarette are matched, thereby avoiding the problem that damages on the electronic cigarette, for example battery overheat or battery leakage, are caused in a case that the battery assembly and the atomizing assembly, which are not matched, are used in combination. In addition, the present application also avoids a poor user experience resulting from the mixed use of the existing battery assembly and atomizing assembly in any combination, the mixed use of tobacco liquids having different flavors, and the mixed use of the battery assembly and the atomizing assembly from different manufacturers. Thus, the present application may facilitate the recognition of the user of the manufactures and brands, and is more beneficial for the user to quit smoking.

The above embodiments are described in a progressive manner. Each of the embodiments is mainly focused on describing its differences from other embodiments, and references may be made among these embodiments with respect to the same or similar portions among these embodiments. For the device in the embodiments, the description thereof is relatively simpler since it is corresponding to the method disclosed in the embodiments, hence, related parts of the device can refer to the description of the method.

Based on the above description of the disclosed embodiments, the person skilled in the art is capable of carrying out or using the present application. It is obvious for the person skilled in the art to make many modifications to these embodiments. The general principle defined herein may be realized in other embodiments without departing from the spirit or scope of the present application. Therefore, the present application is not limited to the embodiments illustrated herein, but should be defined by the broadest scope consistent with the principle and novel features disclosed herein.

The invention claimed is:

1. A battery assembly, applicable for coupling with an atomizing assembly to form an electronic cigarette, wherein the battery assembly comprises:
   a magnetic sensor arranged on the battery assembly and configured to obtain information to be identified contained in a magnetic material of the atomizing assembly; and
   a microcontroller connected to the magnetic sensor, and configured to control a circuit between the battery assembly and the atomizing assembly to be switched on in a case that the microcontroller determines that the information to be identified matches a preset information, to enable the electronic cigarette to work normally; and
   wherein the battery assembly comprises a lower electrode assembly configured to be electrically connected with the atomizing assembly, and the lower electrode assembly comprises an inner electrode which is sleevedly engaged to an outer electrode, the inner electrode is mounted in the battery assembly via an insulating ring, and the magnetic sensor is mounted on an end surface of the inner electrode of the battery assembly.

2. The battery assembly according to claim 1, wherein the magnetic sensor is a magnetic head and/or a Hall sensor.

3. The battery assembly according to claim 1, further comprising:
   a power supply management circuit, arranged between a battery and a magnetic information identification circuit in the battery assembly and configured to manage charging the battery via an external power supply.

4. The battery assembly according to claim 1, wherein the battery assembly further comprises:
   a notification device, electrically connected to a microprocessor and configured to show a matching result from the microprocessor, and the notification device is an alarm or an indicator light.

5. An atomizing assembly, applicable for coupling with a battery assembly to form an electronic cigarette, wherein the atomizing assembly is provided with a magnetic material containing information to be identified and configured to match the battery assembly; and
   wherein the atomizing assembly comprises an upper electrode assembly configured to be electrically connected with the battery assembly, and the upper electrode assembly comprises an outer electrode and an inner electrode which are sleevedly engaged, and the magnetic material to be identified is arranged on the inner electrode.

6. The atomizing assembly for the electronic cigarette according to claim 5, wherein the information to be identified of the magnetic material comprises a magnetic strength and a magnetic signal.

7. An electronic cigarette, comprising a battery assembly and an atomizing assembly, wherein the atomizing assembly is provided with a magnetic material containing information to be identified, and the battery assembly comprises:
   a magnetic sensor arranged on the battery assembly and configured to obtain the information to be identified; and
   a microcontroller connected to the magnetic sensor, and configured to control a circuit between the battery assembly and the atomizing assembly to be switched on in a case that the microcontroller determines that the information to be identified matches a preset information, to enable the electronic cigarette to work normally; and
   wherein the atomizing assembly comprises an upper electrode assembly configured to be electrically connected with the battery assembly, and the upper electrode assembly comprises an outer electrode and an inner electrode which are sleevedly engaged, and the magnetic material to be identified is arranged on the inner electrode.

8. The electronic cigarette according to claim 7, wherein the magnetic sensor is a magnetic head and/or a Hall sensor.

9. The electronic cigarette according to claim 7, wherein the battery assembly further comprises a power supply management circuit, arranged between a battery and a magnetic information identification circuit in the battery assembly and configured to manage charging the battery via an external power supply.

10. The electronic cigarette according to claim 7, wherein the battery assembly further comprises:
    a notification device, electrically connected to a microprocessor and configured to show a matching result from the microprocessor, and the notification device is an alarm or an indicator light.

11. The electronic cigarette according to claim 7, wherein the information to be identified of the magnetic material comprises a magnetic strength and a magnetic signal.

* * * * *